US010119912B2

(12) United States Patent
Mattioli Della Rocca et al.

(10) Patent No.: US 10,119,912 B2
(45) Date of Patent: Nov. 6, 2018

(54) APPARATUS FOR USE IN LUMINESCENCE APPLICATIONS (71) Applicant: STMicroelectronics (Research & Development) Limited, Marlow, Buckinghamshire (GB)

(72) Inventors: Francescopaolo Mattioli Della Rocca, Edinburgh (GB); John Kevin Moore, Edinburgh (GB)

(73) Assignee: STMicroelectronics (Research & Development) Limited, Marlow, Buckinghams (GB)

( * ) Notice: Subject to any disclaimer, the term of this patent is extended or adjusted under 35 U.S.C. 154(b) by 0 days.

(21) Appl. No.: 15/805,322

(22) Filed: Nov. 7, 2017

(65) Prior Publication Data

US 2018/0080875 A1    Mar. 22, 2018

Related U.S. Application Data (63) Continuation of application No. 15/150,559, filed on May 10, 2016, now Pat. No. 9,851,302.

(30) Foreign Application Priority Data

Dec. 18, 2015 (EP) .................................... 15201144

(51) Int. Cl.
*G01N 21/64* (2006.01)

(52) U.S. Cl.
CPC ..... *G01N 21/6428* (2013.01); *G01N 21/6445* (2013.01); *G01N 2021/6439* (2013.01); *G01N 2201/0683* (2013.01)

(58) Field of Classification Search
CPC ........... G01N 21/6458; G01N 21/6428; G01N 21/6445; G01N 21/0683; G01N 2021/6439; G01N 2201/0683
See application file for complete search history.

(56) References Cited

U.S. PATENT DOCUMENTS

| 6,025,917 A | 2/2000 | Toyonaga et al. |
| 8,948,539 B2 | 2/2015 | Meyers et al. |
| 2003/0175987 A1 | 9/2003 | Verdonk et al. |
| 2005/0266147 A1 | 12/2005 | Yao et al. |
| 2006/0012872 A1 | 1/2006 | Hayashi et al. |

(Continued)

FOREIGN PATENT DOCUMENTS

| CN | 103604422 A | 2/2014 |
| JP | 2015141038 A | 8/2015 |

OTHER PUBLICATIONS

EPO Search Report and Written Opinion for EP 15201144.1 dated Jul. 1, 2016 (14 pages).

(Continued)

*Primary Examiner* — David Porta
*Assistant Examiner* — Faye Boosalis
(74) *Attorney, Agent, or Firm* — Crowe & Dunlevy (57) ABSTRACT Photoluminescence from a sample detector is detected using an array of photo-sensitive detectors. At least one first photo-sensitive detector of the array is provided with a first type of linear polarization filter and at least one second photo-sensitive detector is provided with a second type of linear polarization filter. The first type of linear polarization filter has a plane of polarization which is at angled with respect to a plane of polarization of said second type of polarization filter.

19 Claims, 9 Drawing Sheets

(56) References Cited

U.S. PATENT DOCUMENTS

2015/0037877 A1  2/2015  Peng et al.

OTHER PUBLICATIONS

Charanya Tauseef et al: "Trimodal color-fluoresnce-polarization endoscopy aided by a tumor selective molecular probe accurately detects flat legions in colitis-associated cancer" Journal of Biomedical optics, SPIE—International society for optical engineering , US vol. 19, No. 12, Dec. 1, 20147, XP060047214, ISSN:1083-3668, DOI:10.1117/1.JBO.19.12.126002 (retrieved on Dec. 4, 2014) Figures 1(a)-1(b) (15 pages).

Lu H P "Single-Molecule study of protein-protein and protein-DNA interaction dynamics" RNA protein interaction protocols, vol. 305, Jan. 1, 2005, pp. 385-413, XP009059059, ISSN: 1064-3745, Figure 1 (29 pages).

APPARATUS FOR USE IN LUMINESCENCE APPLICATIONS

CROSS REFERENCE TO RELATED APPLICATIONS

This application is a continuation of U.S. patent application Ser. No. 15/150,559 filed May 10, 2016, which claims priority from European Application for Patent No. 15201144.1 filed Dec. 18, 2015, the disclosures of which are incorporated by reference.

TECHNICAL FIELD

Some embodiments relate to an apparatus and in particular but not exclusively to an apparatus for use in luminescence applications, for example, fluorescence imaging applications.

BACKGROUND

Various fluorescence applications are known such as fluorescence anisotropy imaging microscopy (FAIM), and fluorescence lifetime imaging microscopy (FLIM).

Fluorescence anisotropy imaging microscopy (FAIM) concerns the study of molecular orientation and mobility using linearly polarized light. The linearly polarized light preferentially excites fluorophores which have a dipole orientation (absorption transition moment (ATM)) similar to the plane of the electric-field of the linearly polarized light. The fluorophores which have a dipole orientation orthogonal to the plane of the electric-field are not excited, this is known as photo selection. As the fluorophores rotate due to their environment and undergo other processes, the spontaneously emitted light becomes more depolarized. The degree of depolarization that has occurred can be measured by separating the emitted light into orthogonal linear components. The two main contributing factors to the depolarization are rotational diffusion and Förster resonance energy transfer (FRET). This is a particularly useful technique as FAIM can therefore provide spatially resolved information on rotational mobility, molecular binding, or clustering of fluorescently labeled molecules, without dependence on signal intensity.

Anisotropy can be measured using both steady-state FAIM and/or time-resolved FAIM.

With steady-state FAIM, the degree of anisotropy is measured by taking an average of the polarized fluorescence during the excitation time (i.e. exposure time). The steady state FAIM does not allow any information into how the degree of anisotropy changes with respect to time during the excitation (i.e., exposure time). Steady state FAIM is useful to compare cellular systems, as cells with a high degree of proximity will present a lower average degree of anisotropy than cells which are further apart.

Time-resolved FAIM, allows the change in the degree of anisotropy to be measured with respect to time. Upon the excitation of a fluorophore tagged to a cell oriented in the same direction as the incident polarized light, the fluorophore will fluoresce, wherein the fluorescence has a high degree of polarization (i.e. indicating high anisotropy). If the same fluorophore starts coupling energy to neighboring fluorophores tagged to cells that are randomly oriented, the latter fluorophores will start to fluoresce and emit light which has a lower degree of polarization (i.e. indicating low anisotropy). As time passes the degree of anisotropy will therefore decay.

Fluorescence lifetime imaging microscopy (FLIM) is an imaging technique based on differences in the average decay rate of excited states from a fluorescent sample. The contrast in a FLIM image is thus based on the lifetime of individual fluorophores rather than their emission spectra. Unlike intensity measurements, fluorescence lifetime measurements do not depend on: concentration, absorption by the sample, sample thickness, photo-bleaching, and/or excitation intensity.

The fluorescence lifetime of a fluorophore is the average decay rate of excited states from a fluorescent sample, and is characteristic for each fluorescent molecule. As a result, it can be used to characterize a sample. The fluorescent lifetime, however, is dependent on the local environment of the fluorophore, including: FRET, quenching, molecular rotation pH, ion or oxygen concentration, molecular binding or proximity of energy acceptors, as such it is possible to ascertain a wealth of information from the fluorophore by measuring its lifetime. FLIM is often used to observe a change, typically a reduction, in the fluorescence lifetime of a donor, when different fluorophores are in close proximity.

FRET is a process which describes the non-radiative transfer of energy between two similar energy systems that lie physically close together. For example, a donor fluorophore, which is initially in an excited state may transfer energy to an acceptor fluorophore through non-radiative dipole-dipole coupling. In doing so, the acceptor enters an excited state, with the donor becoming quenched. The efficiency of this energy transfer is extremely sensitive to small changes between the distance of the donor and acceptor, and is inversely proportional to the sixth power of that distance. This results in changes to the fluorescence intensity and the fluorescence lifetimes of the two fluorophores.

Two forms of FRET which are of importance are homo-FRET and hetero-FRET. In homo-FRET, only one type of fluorophore is present, as such the energy transfer is reversible. This results in the fluorescent emission form the fluorophore having largely the same polarization as that of the incident excitation beam. In hetero-FRET, two types of fluorophores are present (for example, A, B), as such the fluorophores become mixed into a combination of pairs, for example AA, AB, BA, and BB. If the excitation is tuned to the absorption peak of A, the fluorescence consists of contributions from A (homo-FRET), and B (hetero-FRET). The homo-FRET and hetero-FRET emission may be spectrally separated and thus the hetero-FRET signal is more depolarized than the homo-FRET signal. In hetero-FRET, the fluorescence lifetime of the donor changes as a function of distance between the donor and acceptor, typically the closer the acceptor is to the donor, the shorter the fluorescence lifetime of the donor.

Typically FAIM (both steady-state, and time-resolved) is used to measure homo-FRET, while FLIM is typically used to measure hetero-FRET.

Currently, the systems used in this field are both bulky and expensive. Some embodiments aim to address or at least mitigate this.

SUMMARY

According to a first aspect there is provided a detector for detecting photoluminescence from a sample, the detector comprising: an array of photo-sensitive detectors configured to receive photoluminescence, at least one photo-sensitive detector being provided with a first type of linear polarization filter and at least one photo-sensitive detector being provided with a second type of linear polarization filter, wherein the first type of linear polarization filter has a plane of polarization which is angled with respect to a plane of polarization of the second type of polarization filter.

The first type of linear polarization filter may have a plane of polarization which is at or substantially at right angles to a plane of polarization of the second type of polarization filter.

The detector may be used to detect fluorescence.

Each photo-sensitive detector may be a SPAD.

Each photosensitive detector with one of said first and second linear polarization filter is individually provided with said linear polarization filter.

Each linear polarization filter may be provided by a grid of parallel wires, the longitudinal extent of said wires defining the plane of polarization.

The spacing between adjacent wires may be less than a wavelength of light.

At least one photosensitive detector is provided with a wavelength filter.

A first plurality of photosensitive detectors may be provided with a red filter, a second plurality of photosensitive detectors may be provided with a green filter, and a third plurality of photosensitive detectors may be provided with a blue filter.

Each of said first, second, and third plurality of photo-sensitive detectors comprise at least one photosensitive detector with the first type of linear polarization filter and at least one photosensitive detector with the second type of linear polarization filter.

At least one photosensitive detector may be provided with no wavelength filter.

At least one photosensitive detector may be provided with no linear polarization filter.

Each of said first, second, and third plurality of photo-sensitive detectors comprise at least one photosensitive detector with no linear polarization filter.

Each respective filter may cover more than one photo-sensitive detector.

The detector may comprise a signal processor configured to process outputs from said array to provide, using the same detector, fluorescence anisotropy imaging microscopy FAIM information, and fluorescence lifetime imaging microscopy FLIM information.

The processor may be configured to correlate outputs from the photosensitive detectors which have linear polarizers in FAIM techniques, with outputs from the photosensitive detector which have no linear polarizers.

The processor may be configured to correlate outputs from the photosensitive detectors which have no linear polarizers in FLIM techniques, with outputs from the photosensitive detectors which have linear polarizers.

According to another aspect there is provided an integrated circuit comprising the detector as discussed previously.

BRIEF DESCRIPTION OF THE DRAWINGS

Some embodiments will now be described by way of example only and with reference to the accompanying Figures in which.

DETAILED DESCRIPTION

Figure 1A:
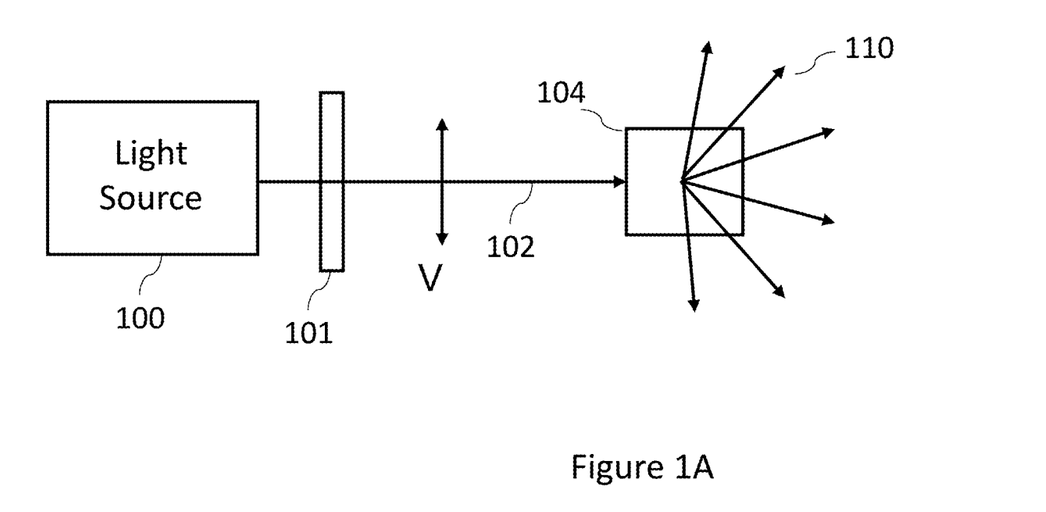
FIG. 1A schematically shows the principles used in some embodiments.

Reference is made to FIG. 1A which shows the principles used in some embodiments. Light from a light source 100 is emitted and passes through a linear polarizer 101. The linear polarizer 101 will cause the unpolarized light emitted by the light source 100 to be linearly polarized (Vertical-polarization in the example shown), V-polarization. The vertically polarized light 102 is then directed onto a sample 104, which for example, may be in a cuvette, or for example, may be on a microscope slide. If, for example, the sample 104 is optically excited at an appropriate wavelength (i.e., with a photon energy higher than the lowest unoccupied molecular orbital, or other similar mechanism) by the vertically polarized light 102, the sample 104 will subsequently emit light 110 which is unpolarized. The light emitted from the sample 110, may for example be, fluorescence.

Figure 1B:
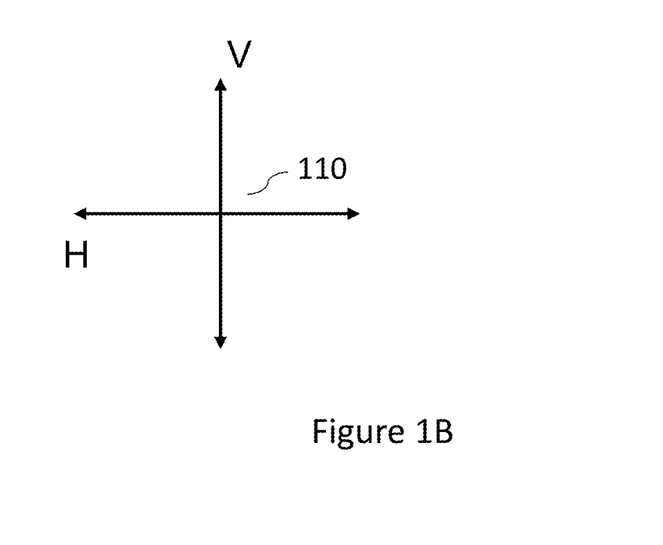
FIG. 1B shows schematically the horizontal and vertical polarization components.

Reference is made to FIG. 1B, the optical emission (unpolarized light) 110 emitted by sample 104, will have both vertical and horizontal planar components. The intensity of the planar components (for example vertical, or horizontal) of the light emitted 110 by the sample 104, may provide intracellular information of the sample 104.

Figure 2:
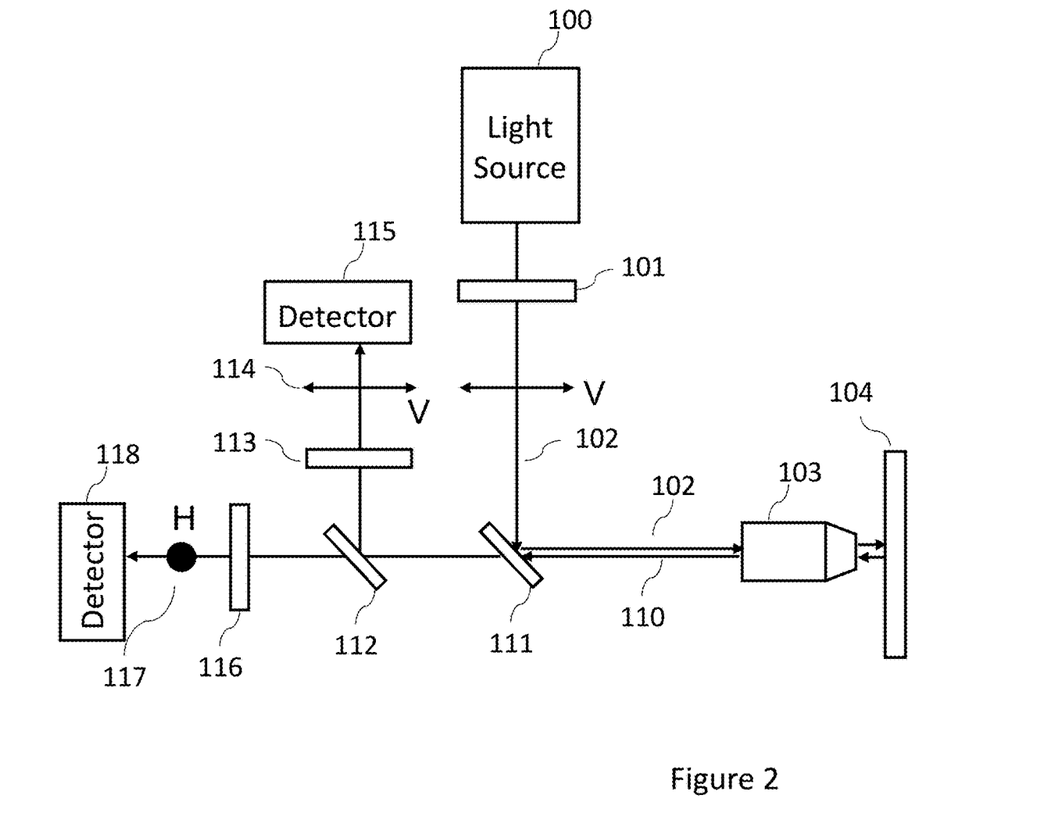
FIG. 2 schematically shows a system.

Reference is now made to FIG. 2 which schematically shows a system. Light from the light source 100 is emitted and passes through a first linear polarizer 101. The linear polarizer 101 will cause the unpolarized light emitted by the light source 100 to be linearly polarized, for example, vertically polarized. The vertically polarized light 102 is then directed via a first beam splitter 111 onto a sample 104, for example through a microscope objective 103. The optical emission 110 from the sample 104, which will be unpolarized, may then be collected by the microscope objective 103. The unpolarized optical emission 110 may then be passed through the first beam-splitter 111. The first beam-splitter 111 may for example have dichroic properties which may filter the wavelength of the optical emission 110, to a desired wavelength range. In some embodiments a monochromator, or other wavelength filtering apparatus may for example be used. The unpolarized optical emission 110 may then be passed through a second beam-splitter 112, which may for example, have a 50:50 transmission to reflection ratio.

The reflected unpolarized optical emission 110 may then be passed through a linear polarizer 113. The linear polarizer 113, for example, may only transmit the vertically polarized components 114 of the optical emission 110 from the sample 104. Accordingly, only the vertically polarized components 114 of the optical emission 110 from the sample 104, will reach the detector 115, and hence be measured.

The transmitted unpolarized optical emission 110 may then be passed through a linear polarizer 116. The linear polarizer 116, for example, may only transmit the horizontally polarized components 117 of the optical emission 110 from the sample 104. Accordingly, only the horizontally polarized components 117 of the optical emission 110 from the sample 104, will reach the detector 118, and hence be measured.

Figure 3:
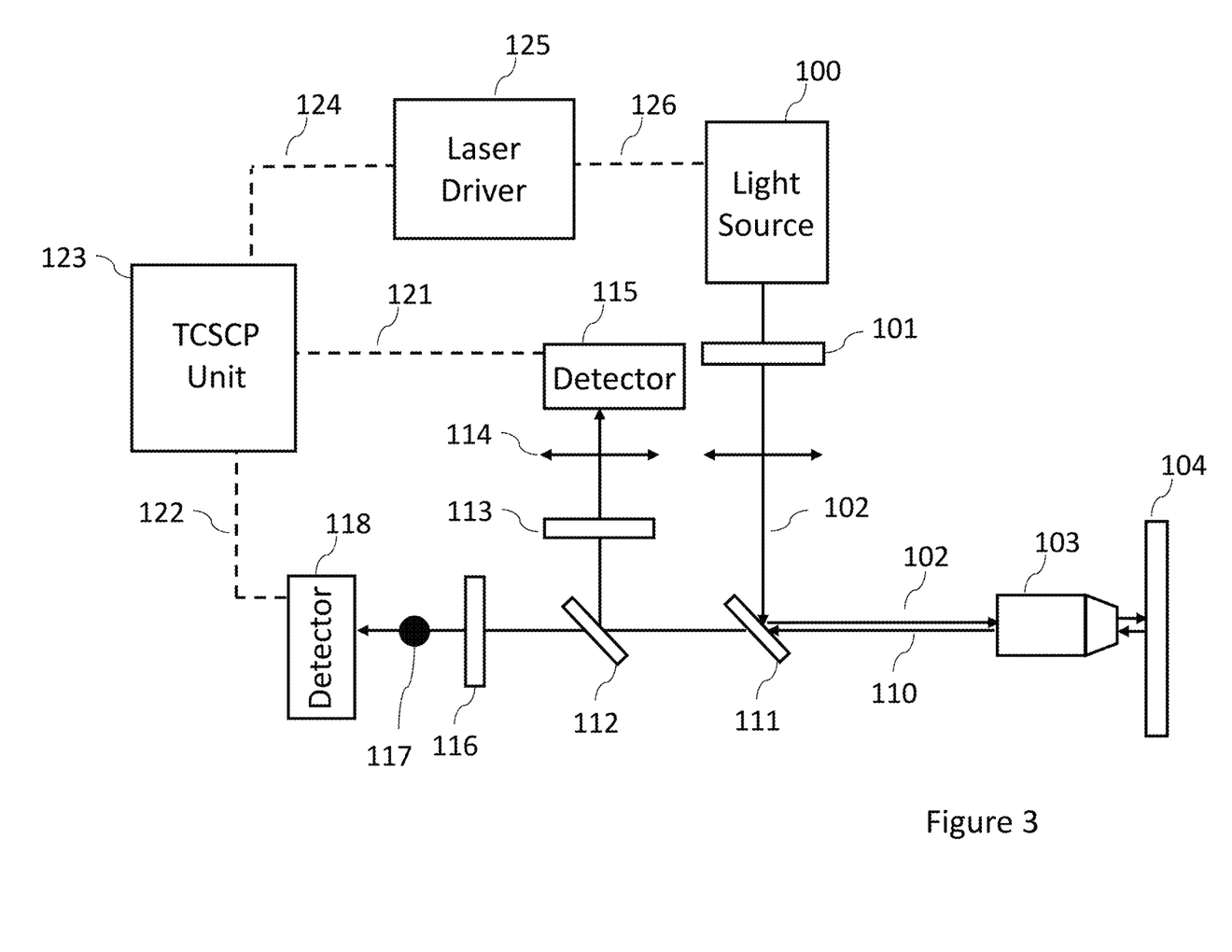
FIG. 3 schematically shows a second system.

Reference is now made to FIG. 3 which shows a second system. In this example, the light 102 emitted from the light source 100 may be pulsed. If, for example, the sample 104 is excited with a pulsed light source 100, the optical emission 110 from the sample 104 will also be pulsed. If the decay time of the pulsed light source 100 is sufficiently short (for example, less than a nanosecond), and the response time of the detectors 115, and 118 is fast enough, the lifetime of the optical emission 110 may be measured. This, for example, may be accomplished using a Time-Correlated Single Photon Counting (TCSPC) technique, using a TCSPC unit 123. The laser driver 125 may trigger the light source 100 to emit a pulse of light using a trigger signal 126. The laser driver may in turn be controlled by the TCSP unit 123 using a control signal 124. In some embodiments, other techniques may be used to pulse modulate the light emitted from the source, for example an acoustic-optical modulator (AOM) in the beam path, or for example a Q-switched laser system, or similar. The pulse of light may then be directed onto the sample 104, with the respective vertical 114 and horizontal 117 components, of the sample's 104 optical emission 110, being detected at detectors 115 and 118 respectively as discussed above and reporting their respective detection data 121 and 122 to the TCSPC unit 123. Correlating the time at which the light source 100 was triggered by the laser driver 125, with the optical emission 110 detected at detectors 115 and 118 respectively, may allow the lifetime of the optical emission 110 to be measured. It may also be possible, for example, to measure the lifetime of the vertical components 114, and the vertical components 117 of the optical emission 110 separately.

For example, in using the techniques described above it may be possible to measure the lifetime of both homo-Forster Resonance Energy Transfer (FRET) and hetero-Forster Resonance Energy Transfer (FRET) between spectrally different fluorophores. However, these techniques are cumbersome, and measuring the lifetime of the excited states of the fluorophores using FLIM, would require a third detector without polarizers. More equipment would be needed to further separate these signals spectrally, such as a monochromator, or colored filters.

Figure 4:
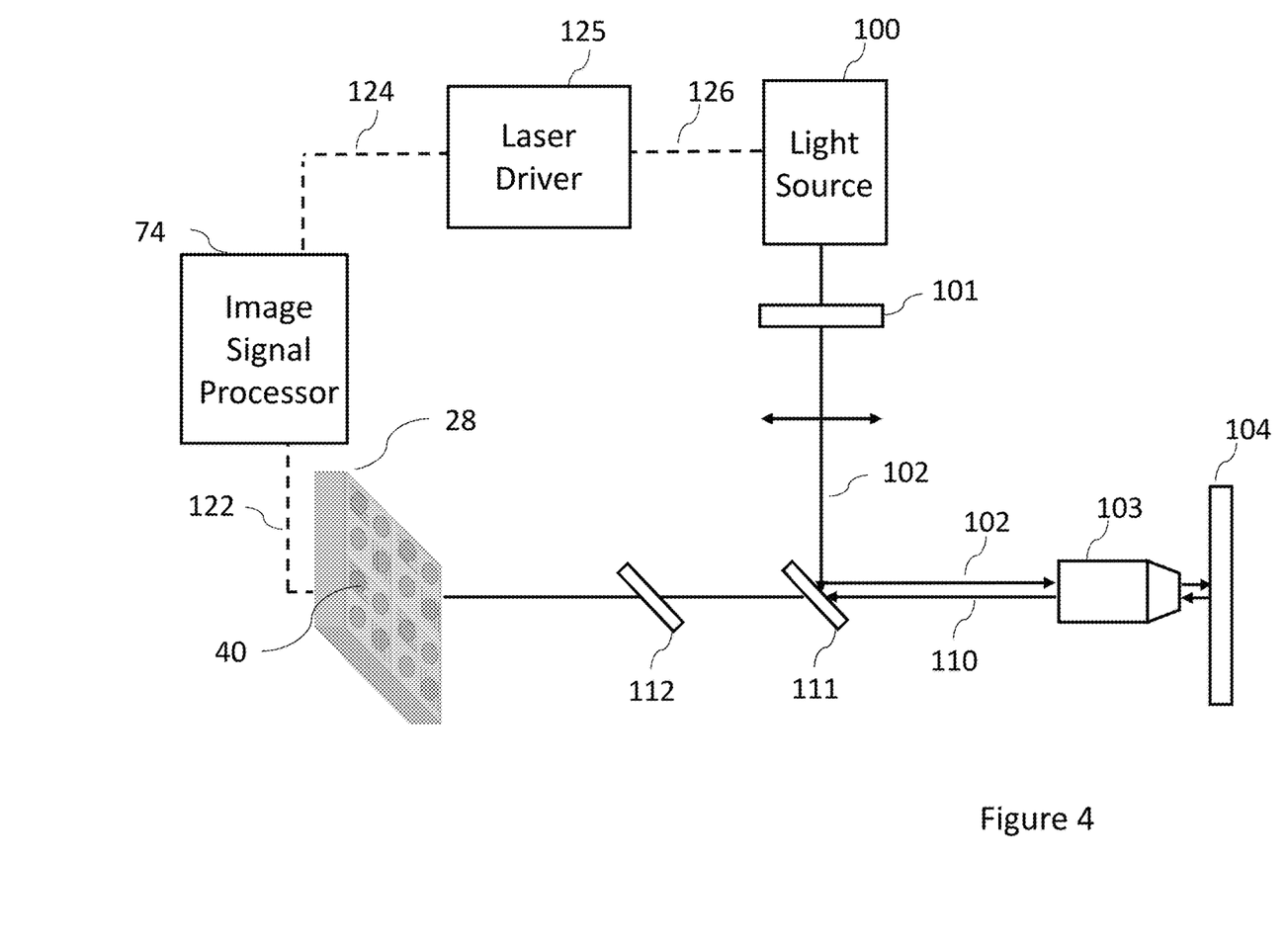
FIG. 4 schematically shows a third system using a single detector.

Reference is now made to FIG. 4, which shows a similar arrangement as discussed above but which uses, for example, only a single detector 28, which may be used for FAIM and FLIM. The signal from the detector, may be passed to an image signal processor 74, which may process the information into a desirable output. If only a single detector 28 is used, the complexity of signal processing performed within the processor 74 required to separate the signals is increased.

In some embodiments, the detector 28 may use single photon avalanche diodes (SPAD) to sense the reflected light. In general, an array of SPADs are provided as a sensor in order to detect a reflected light pulse or light. A photon may trigger an avalanche current in one or more of the SPADs in an SPAD array. The avalanche current may signal an event, namely that a photon of light has been detected.

SPADs operate as follows. At an initial time, the diode is reverse-biased to a voltage larger than its breakdown voltage. The reception of a photon in the diode junction area starts an avalanche current in the diode, which creates an electric pulse. The diode is then biased back to a voltage smaller than the breakdown voltage to quench the avalanche current, so that the SPAD may again react to the reception of a photon. However, the diode must again be reverse-biased to a voltage larger than its breakdown voltage in order to react to another photon. SPADs can currently be used in cycles having reactivation periods shorter than 10 ns.

The detector 28 may comprise one or more SPADs. In some embodiments, an array of SPADs will be provided. As will be discussed in more detail later, some or all of the SPADs will have a linear polarizing filter 40.

Figure 5A:
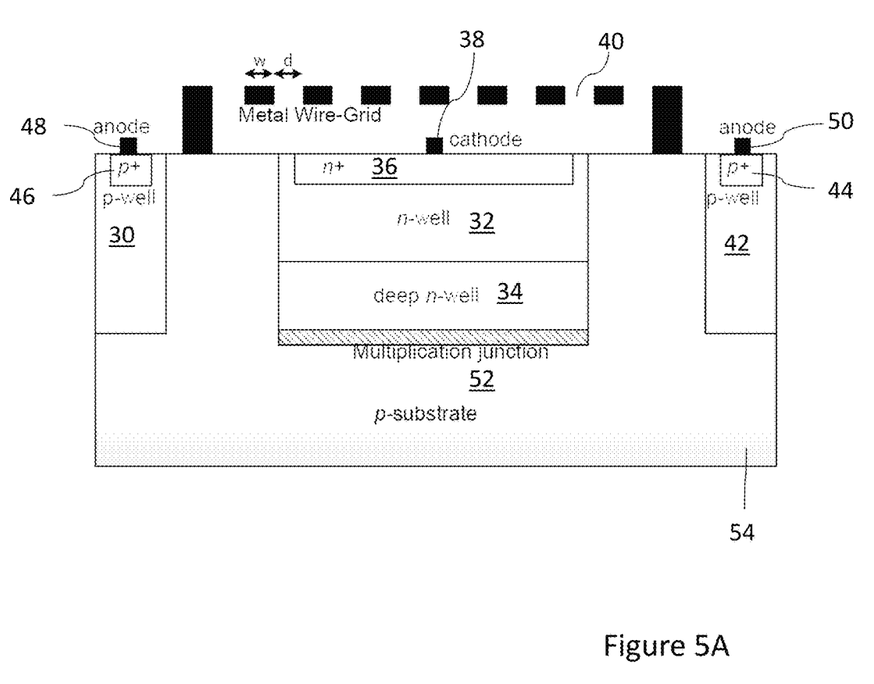
FIG. 5A shows a cross section of a SPAD device used in some embodiments.

Reference is made to FIG. 5A which schematically shows a cross section of a SPAD used in some embodiments. The SPAD 54 may be provided in a p-substrate 52. Respective p wells 30 and 42 may be provided in the substrate. Between the two p-wells 30 and 42 is provided an n-well region. The n-well region comprises a deep n-well 34, an n-well 32 and an n+ region 36. The n+ region 36 is adjacent the surface region of the SPAD and has a cathode 38 in contact therewith. Each of the p-wells 30 and 42 is provided with a respective p+ region 46 and 44. A respective anode 48 and 50 is provided in contact with the respective p+ region 46 and 44. It should be appreciated that a multiplication junction is provided between the deep n-well 34 and the p-substrate 52.

Figure 5B:
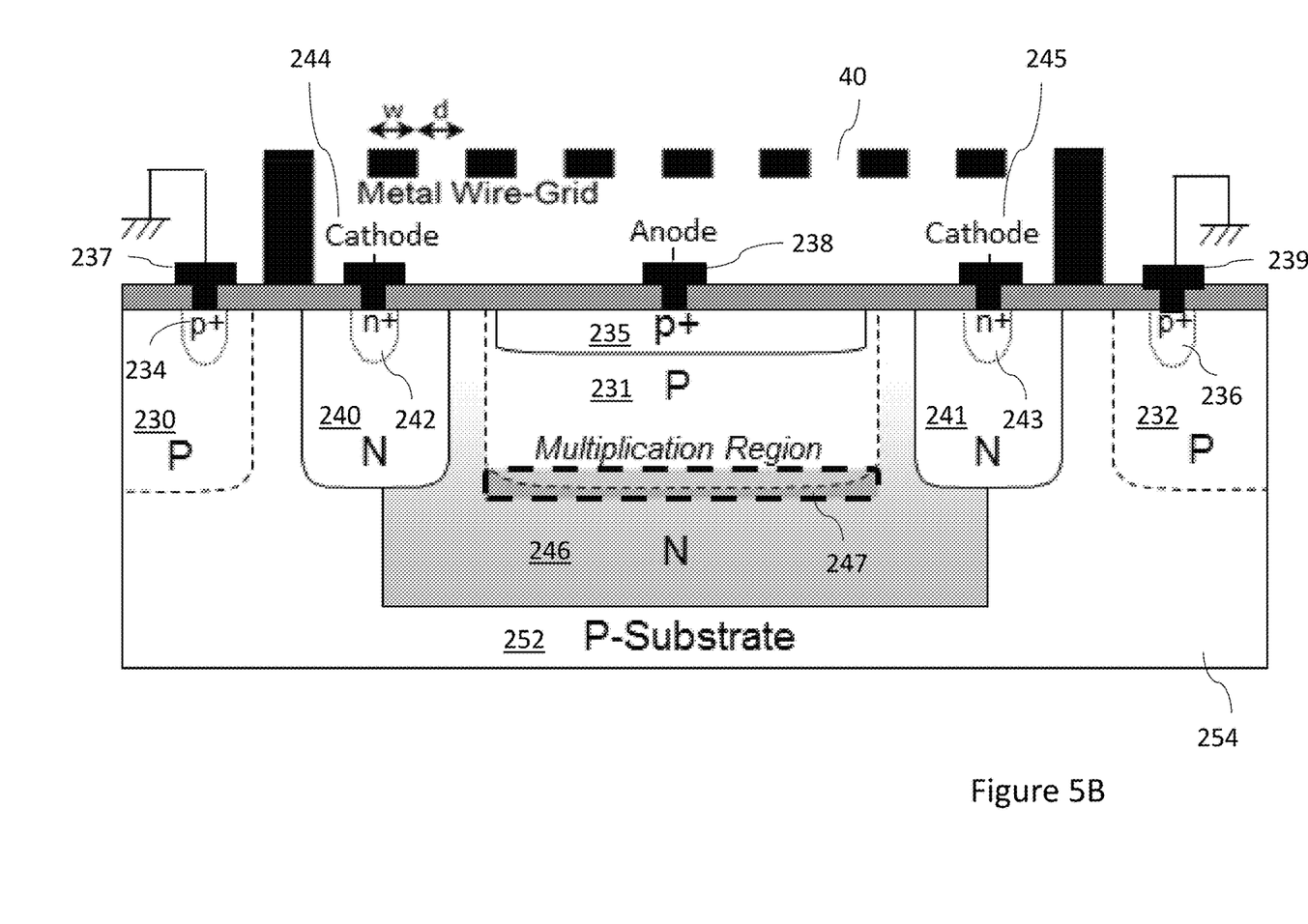
FIG. 5B shows a cross section of a second SPAD device used in some embodiments.

Reference is now made to FIG. 5B which schematically shows a cross section of a SPAD used in some embodiments. The SPAD 254 may be provided in a P-substrate 252. Respective P-wells 230, 231 and 232 may be provided in the substrate. Each of the P-wells 230, 231 and 232 comprise a p+ region 234, 235 and 236. A respective anode 238 is provided to the p+ region 235. Each of the p+ regions 234 and 236 are provided with electrical grounding 237 and 239. The N well regions 240 and 241 are provided respectively between the P well regions 230 and 231 and between the P well regions 23, and 232 (i.e. in a P-N-P-N-P arrangement). Each of the N-wells 240 and 241 comprise an n+ region 242 and 243, respectively. The N wells 240 and 241 are provided with cathodes 244 and 245, respectively. The N-P-N wells 240, 231 and 241, respectively, are provided with a deep N-well 246. A multiplication junction 247 is provided between the deep N-well 246 and P well 231. In some embodiments the linear polarizer grid edges 248 should contact from top metal down to Poly, to avoid side illumination.

A closely spaced metal wire grid 40 is provided over the surface of the SPAD and is thus between the SPAD detector and the source of the reflections. The wire grid has a plurality of parallel wires. The closely spaced wire grid acts as a polarization filter for light. The spacing d between the wires may be smaller than the wavelength of light and may for example be: $d=\lambda/2$ (where $\lambda$ is wavelength). The width w of the wire may be as small as the process allows: w=minimum (where w is the wire width, where the wire may for example be made of metal), the value of w may for example be 0.14 μm.

In some embodiments, a wire grid filter may be provided on each individual SPAD.

It should be appreciated that the orientation of the wires controls the direction of the linear polarization provided by the grid.

Figure 6:
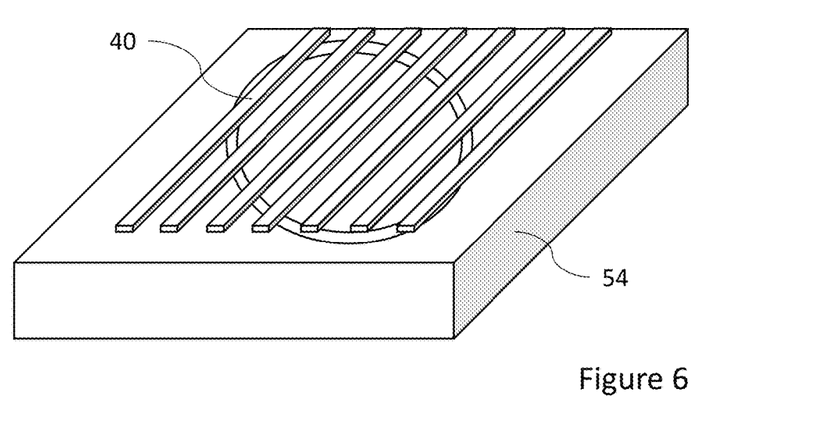
FIG. 6 shows a perspective view of the SPAD device of FIGS. 5A-5B.

In this regard, reference is made to FIG. 6 which schematically shows the grid 40 provided on the SPAD 54. In some embodiments, it is ensured that the grid end edges, in the longitudinal direction parallel to the wires, should contact from the top metal down to the poly layer to avoid side illumination impinging on the SPAD, thus bypassing the polarization function provided by the grid. The edges which are perpendicular to the longitudinal direction of the wires do still provide a polarization function. However, in some embodiments, the grid end edges in the parallel direction to the wires may be such that there is a continuous side edge to prevent any side illumination.

Figure 7:
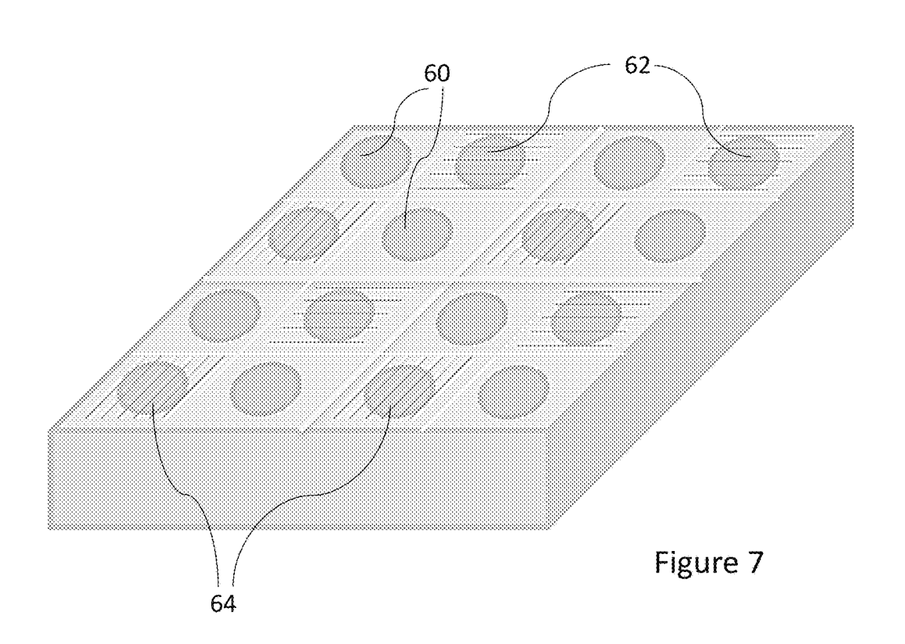
FIG. 7 shows schematically an example of an imager with linear polarization filtering.

Reference is now made to FIG. 7 which schematically shows an arrangement of filters on the SPAD array. In this example, some of the SPADs 60 are without any wire grid and are thus able to detect all light including polarized light. In other words, these SPADs do not have any filter on them. Some of the SPADs 62 are each provided with a wire grid which is oriented in one direction and some of the SPADs 64 are provided with wire grids which are oriented in a direction perpendicular to that of SPADs 62. In the example shown in FIG. 7 those SPADs referenced 62 may for example only detect vertically polarized light whereas as those which are referenced 64 are able to detect only horizontally polarized light.

Figure 8:
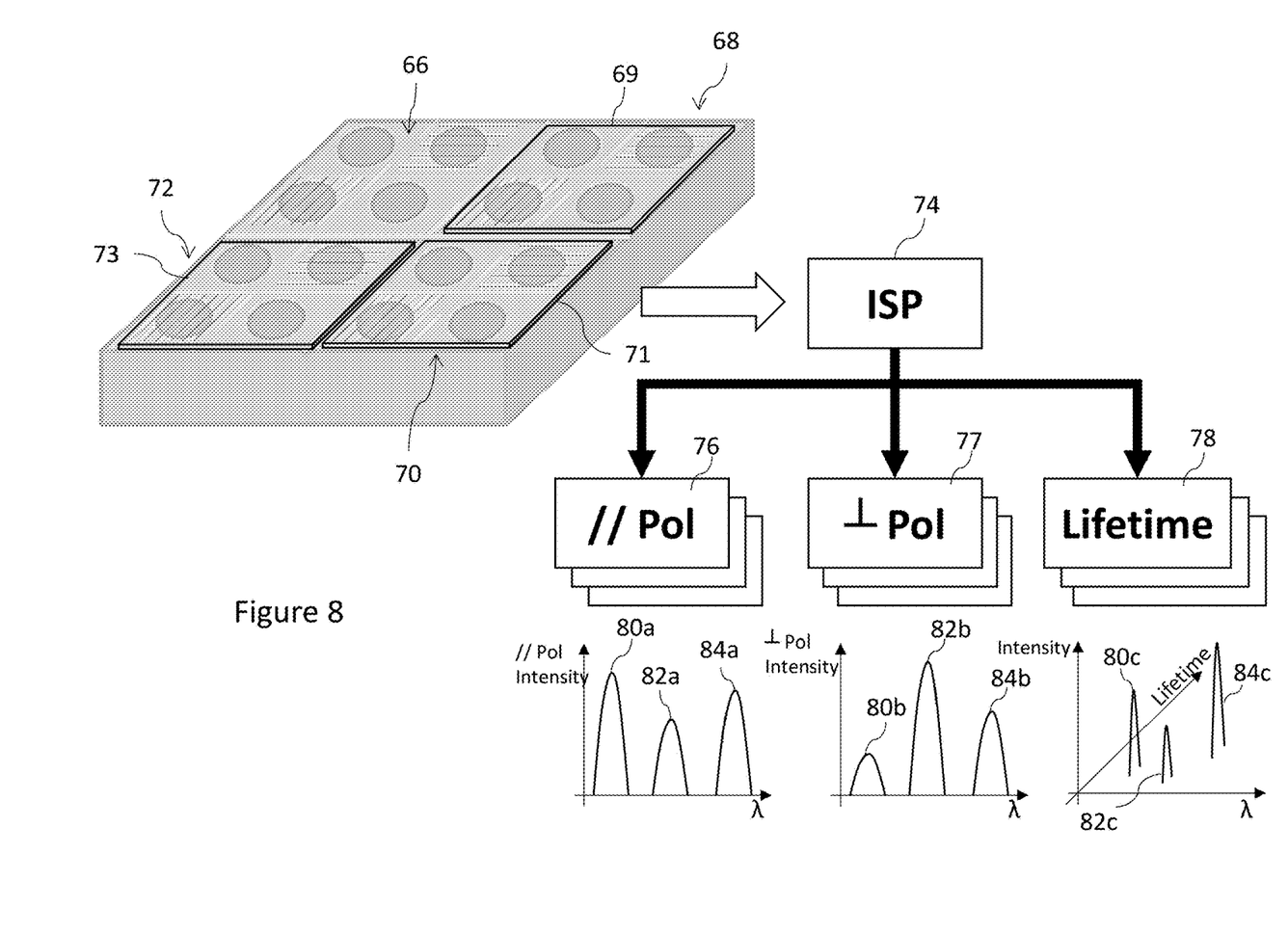
FIG. 8 shows the imager of FIG. 7 with the addition of color filters and schematically shows the associated processing functions.

Reference is made to FIG. 8 which shows a modification to the arrangement shown in FIG. 7. In this example, color filters are additionally provided to allow spectral discrimination. For example, those pixels referenced 66 may have no color filter. The pixels without a color filter 66 may be used to detect spectrally wide band emission (i.e., detect all of the emitted light without spectral filtering). In some embodiments, these pixels 66 may be in an array together with RGB filtered SPADs. In other embodiments, these pixels 66 may be used exclusively.

Those pixels referenced 68 may have a green filter 69, those pixels referenced 70 may have a red filter 71 and those pixels referenced 72 may have a blue filter 73. It should be appreciated that in different embodiments more or less than the three color filters may be provided. It should be appreciated that alternatively or additionally, different colored filters may be used. In some embodiments, the color filters may be provided on an individual pixel basis. Different patterns and positions for the filters may thus be provided in different embodiments.

In some embodiments, the SPADs which have a linear polarizer in-front of them are used to measure homo-FRET in both steady-state and time-resolved FAIM techniques. In other embodiments, the SPADs which do not have a linear polarizer in-front of them may be used in combination or otherwise with the detected polarized light in FAIM techniques, for example as photon counters.

In some embodiments, the SPADs which do not have a linear polarizer in-front of them are used to measure the fluorescence lifetime (hetero-FRET) in FLIM techniques. In other embodiments, the SPADs which do have a linear polarizer in-front of them may be used in combination or otherwise with the detected unpolarized light in FLIM techniques, for example as photon counters.

In some embodiments, SPADs with color filters in-front of them are used to obtain spectrally distinct fluorescence of both homo-FRET, and hetero-FRET, using FAIM and FLIM techniques respectively. In some embodiments these color filters may be red, green, and blue. In other embodiments other types of wavelength filters may be used, for example, dichroic filters, band pass filters, edge filters, notch filters, or the like. In other embodiments SPADs with no color filters in-front of them are used to obtain spectrally wide band emission for both FAIM and FLIM techniques.

Table 1 below shows an example of some embodiments, where an 'X' indicates how information from the detector may be used. 'Pol' indicates that polarization information has been measured, and 'none' indicates that no polarization information has been measured.

TABLE 1

| | Red filter | | Green filter | | Blue filter | | No-color filter | |
|---|---|---|---|---|---|---|---|---|
| | Pol | none | Pol | none | Pol | none | Pol | none |
| FAIM (Homo-FRET) | X | | X | | X | | X | |
| FLIM (Hetero-FRET) | | X | | X | | X | | X |

In some embodiments, information from the SPADs which measure polarized emission are used to measure FAIM, and information from the SPADs which do not measure polarized emission are used to measure FLIM.

It should be appreciated that the information from at least one detector, with or without a filter arrangement, may be used to contribute information to the FAIM and FLIM techniques, using data correlation techniques.

The outputs from the SPAD array is provided to an image signal processor (ISP) 74. The image signal processor is thus able to provide outputs for the vertically polarized light, the perpendicularly polarized light and the fluorescence lifetime. In the ISP 74 the fluorescence lifetime is calculated by fitting the time-resolved fluorescence decay, using FLIM, to an exponential function, wherein the lifetime is equal to the exponential decay constant of the exponential fit. This information is provided for each of the three colors, as well as the wide band pixels. As can be seen, information for each of the different colors may be graphically represented for each of the polarizations. For example, graphs may be provided which show intensity plotted against wavelength ($\lambda$). The peaks referenced 80 are for the blue filtered results, those referenced 82 are for the green filtered results and those referenced 84 are for the red filtered results. The first graph shows the results for the vertical polarization, the second graph shows the results for the horizontal polarization and the third graph shows the results where there is no polarization filter.

Figure 9:
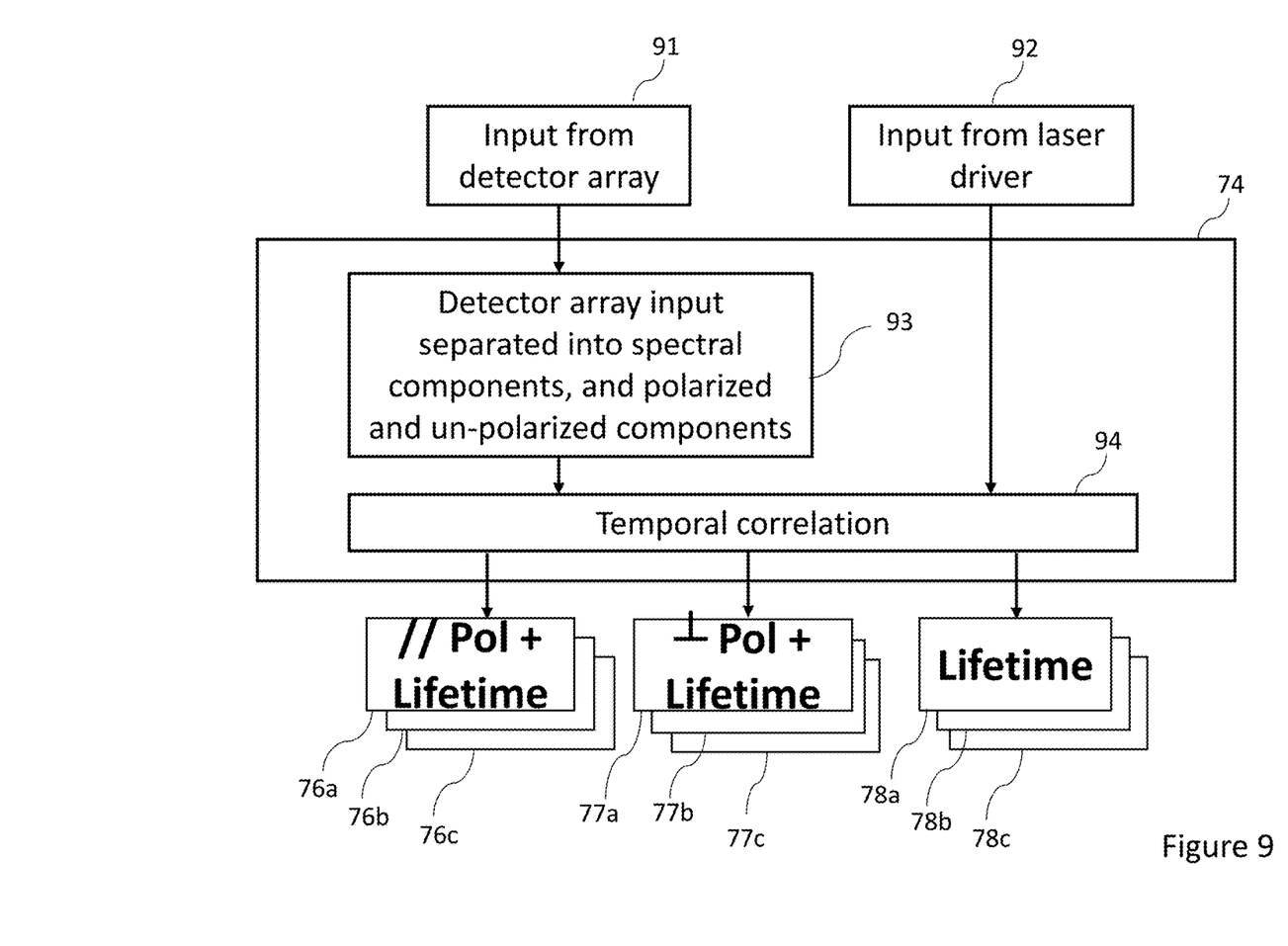
FIG. 9 shows the method of ISP processing when the imager of FIG. 7 is used in the arrangement of FIG. 4.

Reference is now made to FIG. 9, which shows, for example, the processing undertaken by the image signal processor (ISP) 74. The signal generated by the detector depicted in FIG. 8 by references 66, 68, 70 and 72, may then be passed into the ISP 74 as an input from the detector array 91. The timing signal from the laser driver may then also be passed into the ISP 74 as an input from the laser driver 92. The ISP 74, may then separate 93 the spectral, and polarized and un-polarized components of the signal 91 from the detector. This information may then be temporally correlated 94 with the input from the laser driver 92. The ISP 74 may then output the polarized information and lifetime components 76, 77, and 78. The polarized information and lifetime components may then be further separated into their spectral components for example, using the red, green and blue color filters described earlier. For example, the parallel polarized lifetime output 76, may be separated into red 76a, green 76b, and blue 76c. The orthogonal polarized lifetime output may be separated into red 77a, green 77b, and blue 77c. Additionally, the unpolarized lifetime may be separated into red 78a, green 78b, and blue 78c.

It should be appreciated that the information which is captured by the array can be processed in any suitable manner.

It should be appreciated that some embodiments of the invention may allow a compact device to the achieved.

In some embodiments the polarization filters, and/or color filters, may be printed onto one or more transmissive surfaces, for example, silica or quartz, to form an arrayed optical filter. Such an optical filter may then be positioned in-front of an array of SPADs, to achieve a similar effect.

In some embodiments the relationship between filters and photo-sensitive detectors is not one to one. A single filter, for example, a linear polarizer, may cover more than one SPAD, for example four SPADs. Likewise, for example, a single color filter may cover more than one SPAD. It should be appreciated that the number of SPADs, covered or not covered, by at least one of the filters, may vary.

Some embodiments may use other photo-sensitive detectors, instead of SPADs, for example, APDs, photodiodes, or the like. These sensors may be integrating elements generating events on reception of the light information.

It should be appreciated that the above described arrangements may also be used for other photoluminescence applications, for example phosphorescence applications, or Raman spectroscopy. Raman spectroscopy typically being a method of characterizing a substance by reflecting light of a known wavelength from a surface, and measuring small changes in the wavelength of the reflected light.

It should be appreciated that the above described arrangements may be implemented at least partially by an integrated circuit, a chip set, one or more dies packaged together or in different packages, discrete circuitry or any combination of these options.

Various embodiments with different variations have been described here above. It should be noted that those skilled in the art may combine various elements of these various embodiments and variations.

Such alterations, modifications, and improvements are intended to be part of this disclosure, and are intended to be within the scope of the present invention. Accordingly, the foregoing description is by way of example only and is not intended to be limiting. The present invention is limited only as defined in the following claims and the equivalents thereto.

The invention claimed is:

1. A system, comprising:
a light source configured to emit pulses of light directed towards a sample;
a first photo-sensitive detector configured to receive photoluminescence from said sample in response to said pulses of light, said first photo-sensitive detector having a first type of linear polarization filter;
a second photo-sensitive detector configured to receive photoluminescence from said sample in response to said pulses of light, said second photo-sensitive detector having a second type of linear polarization filter;
wherein said first type of linear polarization filter has a plane of polarization which is angled with respect to a plane of polarization of said second type of polarization filter;
wherein each of the first and second linear polarization filters is provided by a grid of parallel wires, wherein a longitudinal extent of said parallel wires defines the plane of polarization; and
a signal processor configured to receive output from the first and second photo-sensitive detectors and further configured to trigger the light source to emit said pulses of light, the signal processor operable to separately measure an optical emission lifetime of a first polarization component of said photoluminescence detected by the first photo-sensitive detector and a second polarization component of said photoluminescence detected by the second photo-sensitive detector.

2. The system as claimed in claim 1, wherein each of the first and second photo-sensitive detectors includes at least one single photon avalanche diode (SPAD) and the separate measures of optical emission lifetime relate to single photon counts of signals output by the SPADs.

3. The system as claimed in claim 1, wherein the measured optical emission lifetime is a lifetime of at least one of homo-Forster Resonance Energy Transfer and hetero-Forster Resonance Energy Transfer.

4. The system as claimed in claim 1, wherein a spacing between adjacent wires in the grid of parallel wires is less than a wavelength of the photoluminescence to be detected.

5. The system as claimed in claim 1, further comprising a colored filter over one of the first and second photo-sensitive detectors, wherein there is no colored filter over the other of the first and second photo-sensitive detectors.

6. A system, comprising:
a light source configured to emit pulses of light directed towards a sample;
a sensor array including at least one first photo-sensitive detector having a first type of linear polarization filter and at least one second photo-sensitive detector having a second type of linear polarization filter, wherein said first type of linear polarization filter has a plane of polarization which is angled with respect to a plane of polarization of said second type of polarization filter;
wherein each photo-sensitive detector in the sensor array having one of said first and second linear polarization filters is individually provided with a linear polarization filter;
a signal processor configured to receive output from the at least one first photo-sensitive detector and the at least one second photo-sensitive detector and further configured to trigger the light source to emit said pulses of light, the signal processor operable to separately measure an optical emission lifetime of a first polarization component of said photoluminescence detected by the at least one first photo-sensitive detector and a second polarization component of said photoluminescence detected by the at least one second photo-sensitive detector, and
a colored filter over one of the first and second photo-sensitive detectors, wherein there is no colored filter over the other of the first and second photo-sensitive detectors.

7. The system as claimed in claim 6, wherein each photo-sensitive detector of the first and second photo-sensitive detectors comprises a single photon avalanche diode (SPAD) and the separate measures of optical emission lifetime relate to single photon counts of signals output by the SPADs.

8. The system as claimed in claim 6, wherein the measured optical emission lifetime is a lifetime of at least one of homo-Forster Resonance Energy Transfer and hetero-Forster Resonance Energy Transfer.

9. The system as claimed in claim 6, wherein each individual linear polarization filter comprises a grid of parallel wires, wherein a longitudinal extent of said parallel wires defines the plane of polarization.

10. The system as claimed in claim 9, wherein a spacing between adjacent wires in the grid of parallel wires is less than a wavelength of the photoluminescence to be detected.

11. A system, comprising:
a light source configured to emit pulses of light directed towards a sample which emits a photoluminescence in response to said pulses of light;
a first splitter configured to receive the emitted photoluminescence and produce a first photoluminescence signal in a first path and a second photoluminescence signal in a second path;
wherein the first path is distinct from the second path;
a first type of linear polarization filter configured to receive the first photoluminescence signal and output a polarized first photoluminescence signal;
a second type of linear polarization filter configured to receive the second photoluminescence signal and output a polarized second photoluminescence signal;
a first photo-sensitive detector configured to receive the polarized first photoluminescence signal;
a second photo-sensitive detector configured to receive the polarized second photoluminescence signal; and
a signal processor configured to receive output from the first and second photo-sensitive detectors and further configured to trigger the light source to emit said pulses of light, the signal processor operable to separately measure an optical emission lifetime of a first polarization component of said photoluminescence from the polarized first photoluminescence signal detected by the first photo-sensitive detector and a second polarization component of said photoluminescence from the polarized second photoluminescence signal detected by the second photo-sensitive detector.

12. The system of claim 11, wherein each of the first and second photo-sensitive detectors includes at least one single photon avalanche diode (SPAD) and the separate measures of optical emission lifetime relate to single photon counts of signals output by the SPADs.

13. The system of claim 11 wherein the polarized first photoluminescence signal output from the first type of linear polarization filter is one of horizontally or vertically oriented, and wherein the polarized second photoluminescence signal output from the second type of linear polarization filter is the other of horizontally or vertically oriented.

14. The system of claim 11, further comprising a second splitter configured to reflect the emitted pulses of light to be directed towards the sample and further configured to pass the emitted photoluminescence through to the first splitter.

15. The system of claim 14, further comprising a third type of linear polarization filter configured to receive the emitted pulses of light output from the light source and produce polarized pulses of light to be directed towards the sample.

16. The system of claim 11, wherein each of the first and second types of linear polarization filters is provided by a grid of parallel wires, wherein a longitudinal extent of said parallel wires defines a plane of polarization.

17. The system of claim 16, wherein a spacing between adjacent wires in the grid of parallel wires is less than a wavelength of the photoluminescence to be detected.

18. The system of claim 11, further comprising a colored filter over one of the first and second photo-sensitive detectors, wherein there is no colored filter over the other of the first and second photo-sensitive detectors.

19. The system of claim 11, wherein each of the first and second photo-sensitive detectors includes at least one single photon avalanche diode (SPAD) and the separate measures of optical emission lifetime relate to single photon counts of signals output by the SPADs.

* * * * *